United States Patent
Oh et al.

(10) Patent No.: US 8,299,804 B2
(45) Date of Patent: Oct. 30, 2012

(54) NONDESTRUCTIVE INSPECTION METHOD OF INSULATOR USING FREQUENCY RESONANCE FUNCTION

(75) Inventors: Ki-Yong Oh, Daejeon (KR);
Joon-Young Park, Daejeon (KR);
Jae-Kyung Lee, Daejeon (KR);
Byung-Hak Cho, Gwangju (KR)

(73) Assignee: Korea Electric Power Corporation, Seoul (KR)

( * ) Notice: Subject to any disclaimer, the term of this patent is extended or adjusted under 35 U.S.C. 154(b) by 250 days.

(21) Appl. No.: 12/806,426

(22) Filed: Aug. 10, 2010

(65) Prior Publication Data
US 2011/0037482 A1  Feb. 17, 2011

(30) Foreign Application Priority Data
Aug. 12, 2009 (KR) .................. 10-2009-0074047

(51) Int. Cl.
*G01R 31/02* (2006.01)

(52) U.S. Cl. ....................................................... 324/551
(58) Field of Classification Search ................ 324/551, 324/537, 555, 557, 541, 544; 340/647
See application file for complete search history.

(56) References Cited

U.S. PATENT DOCUMENTS

| | | | |
|---|---|---|---|
| 3,948,087 A * | 4/1976 | Shiraishi .................... | 73/668 |
| 4,502,329 A * | 3/1985 | Fukunaga et al. ............. | 73/573 |
| 5,883,478 A * | 3/1999 | Thesling ..................... | 318/119 |
| 6,276,536 B1 * | 8/2001 | Terasaki et al. ............... | 209/599 |
| 6,385,553 B1 * | 5/2002 | Naito et al. .................. | 702/138 |
| 2006/0192566 A1 * | 8/2006 | Fleming ..................... | 324/555 |

* cited by examiner

*Primary Examiner* — Hoai-An D Nguyen
(74) *Attorney, Agent, or Firm* — McDermott Will & Emery LLP

(57) ABSTRACT

A nondestructive inspection method of testing insulators using frequency resonance function that can inspect an anomaly of an insulator by vibrating the insulator with a force having the characteristic of white noise, measuring the change in motion of the insulator according to the vibration and calculating the frequency resonance function of the insulator is disclosed.

10 Claims, 14 Drawing Sheets

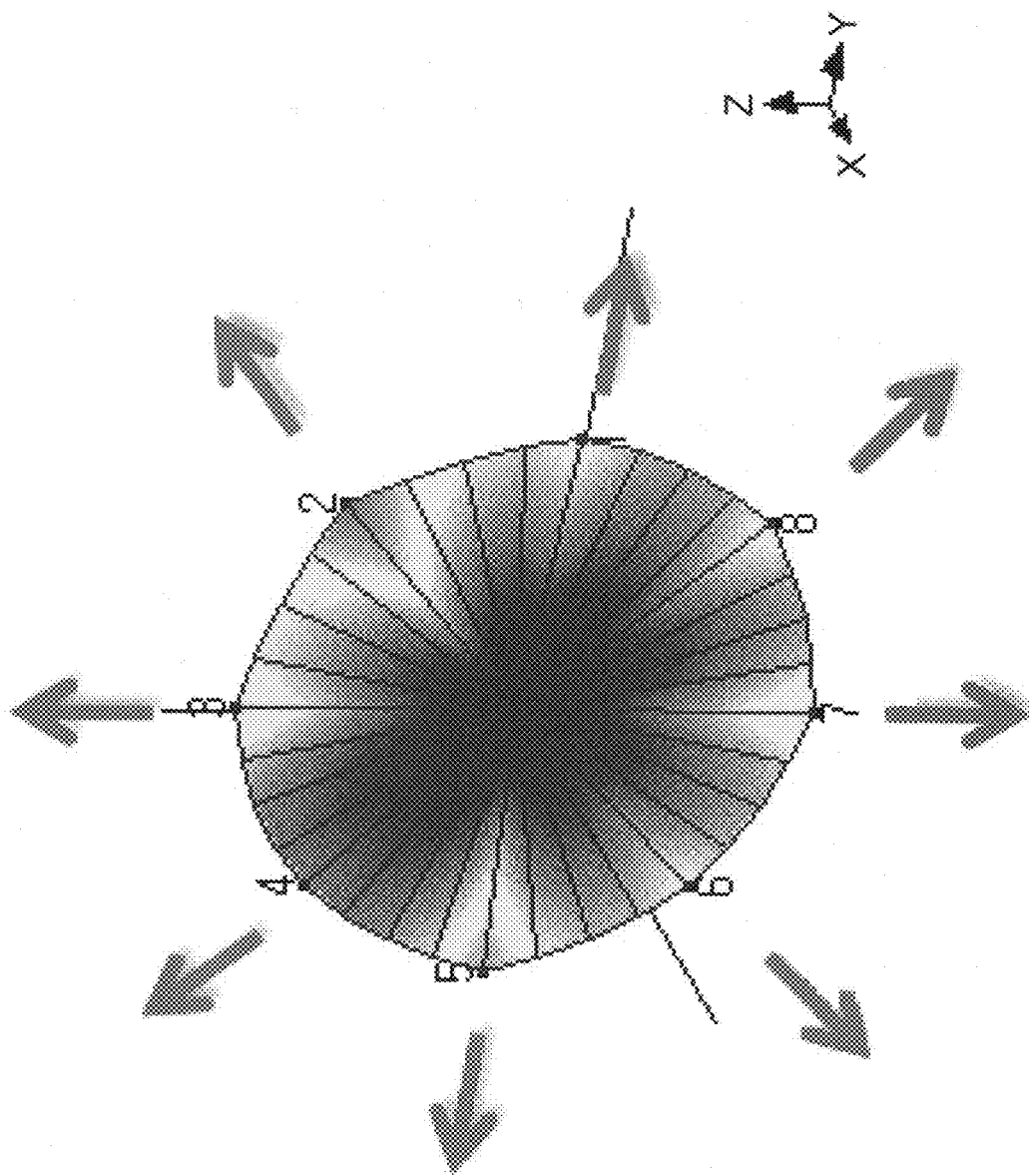

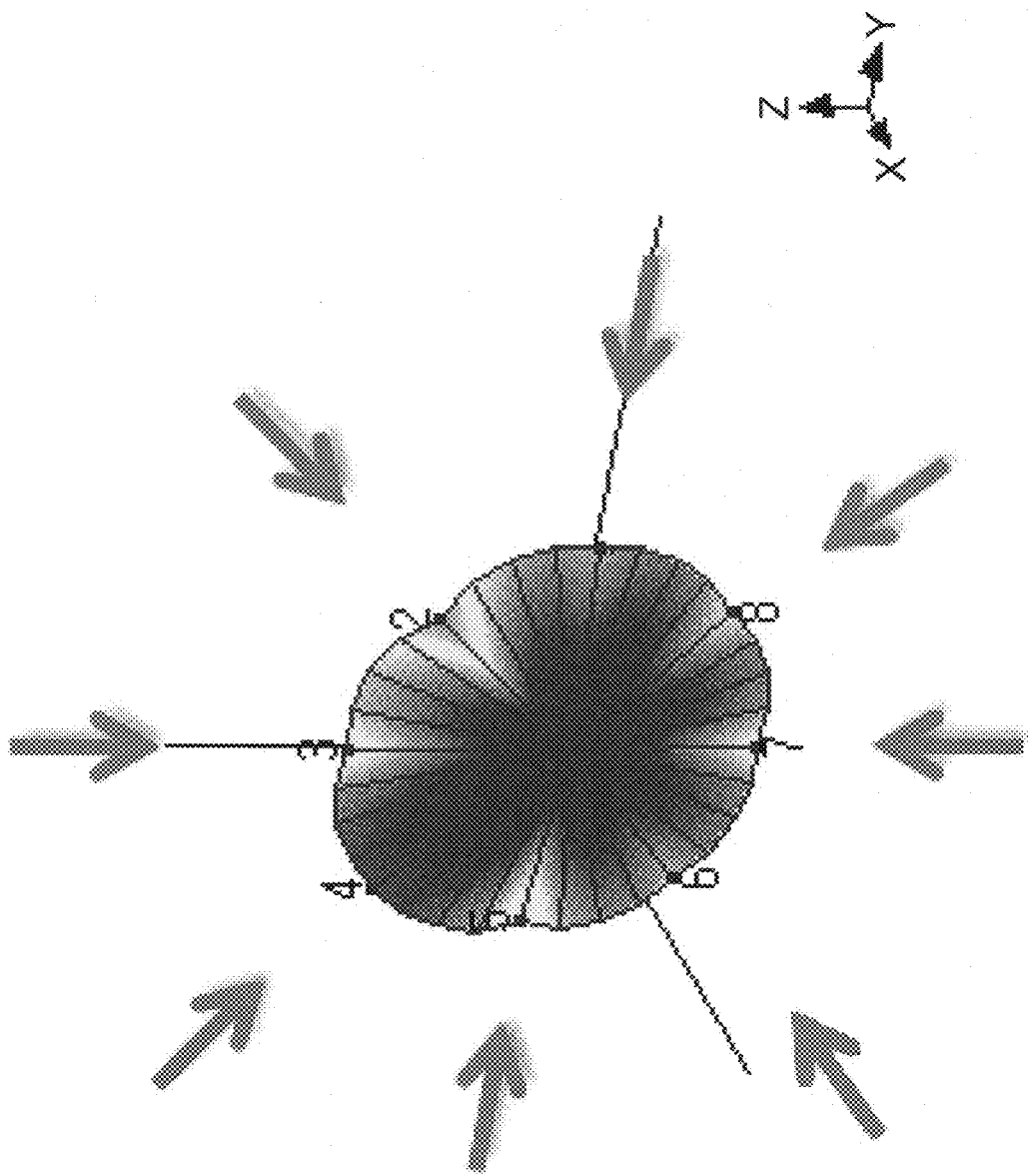

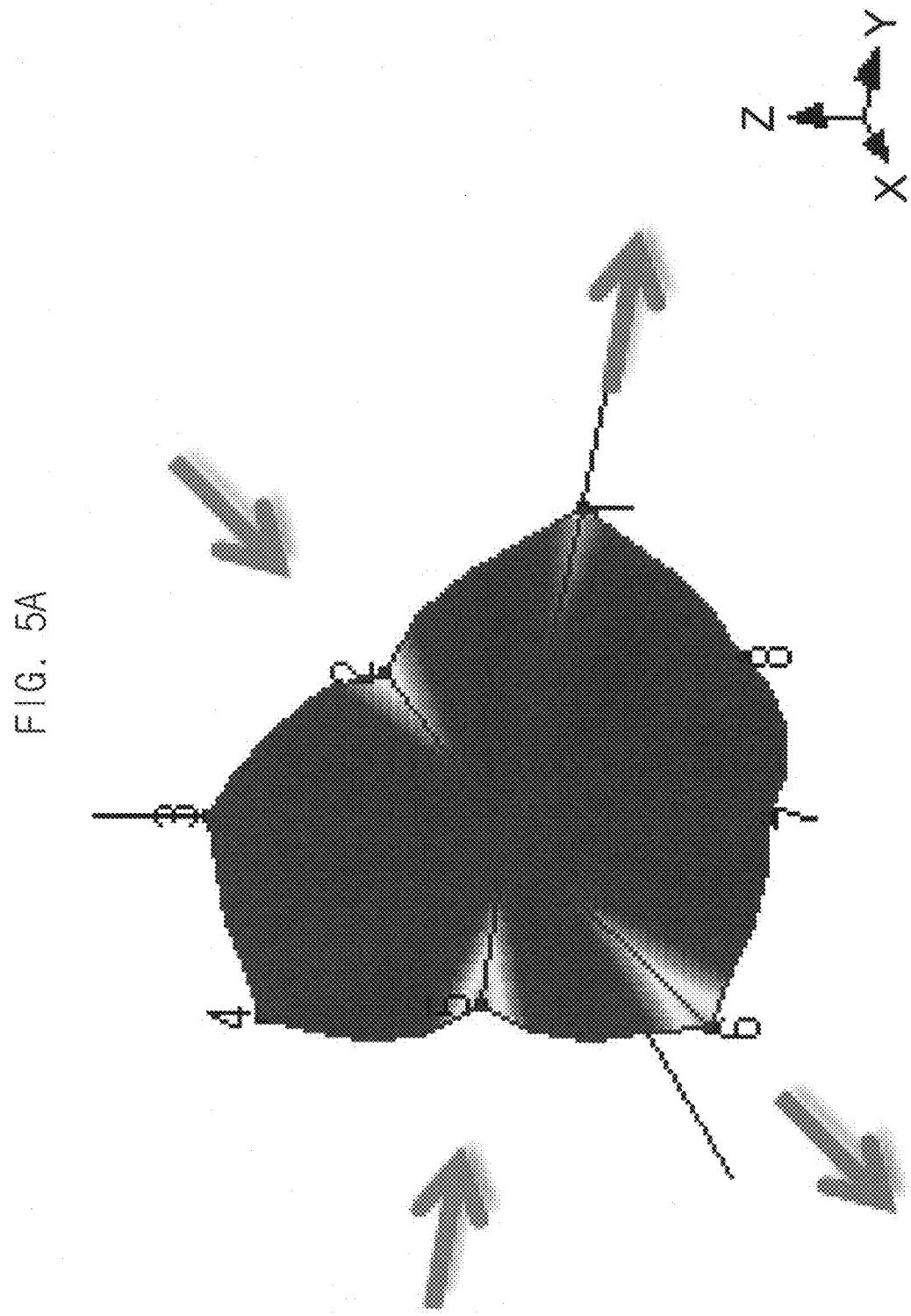

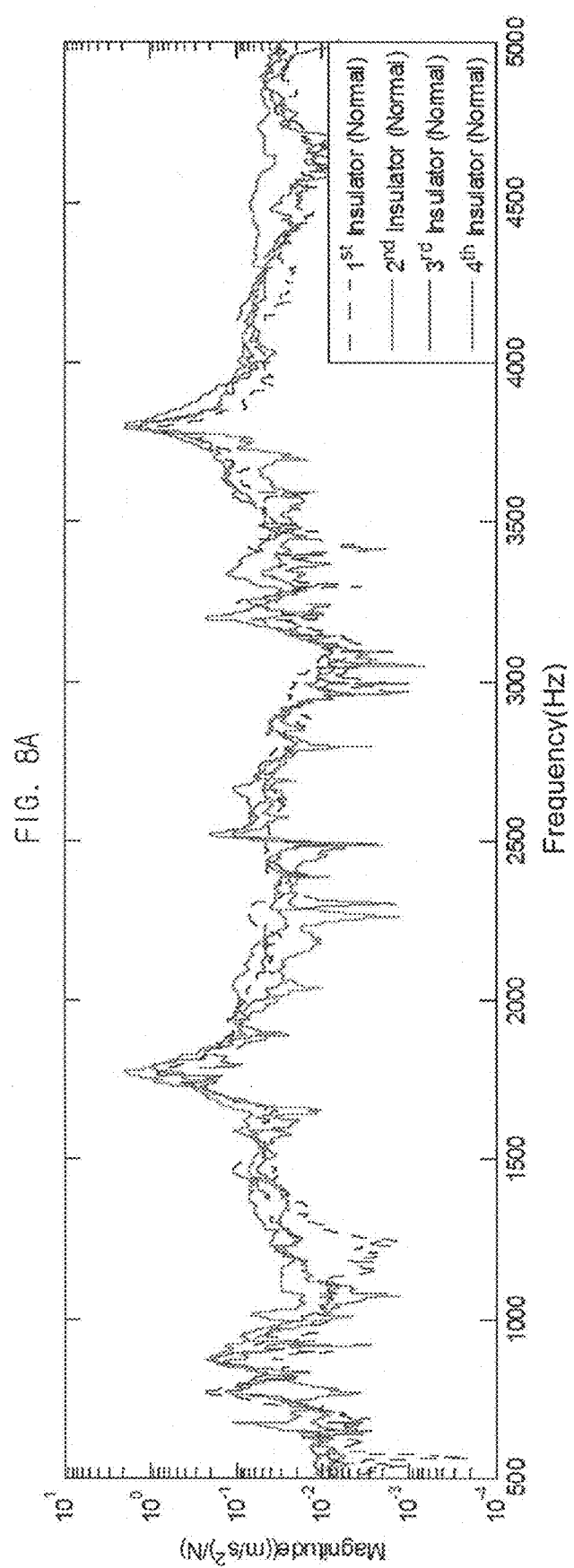

NONDESTRUCTIVE INSPECTION METHOD OF INSULATOR USING FREQUENCY RESONANCE FUNCTION

CROSS-REFERENCE TO RELATED APPLICATIONS

This application claims the benefit of Korean Patent Application No. 10-2009-0074047, filed with the Korean Intellectual Property Office on Aug. 12, 2009, the disclosure of which is incorporated herein by reference in its entirety.

BACKGROUND

1. Technical Field

The present invention relates to a nondestructive inspection method, more specifically to a nondestructive inspection method of testing insulators by using the frequency resonance functions of an insulator being inspected.

2. Description of the Related Art

To inspect anomalies of an insulator, a number of methods including a buzz method, a potential measurement method, a resistance measurement method and a field measurement method have been developed. Among these, a field-type detector for detecting a defective insulator that employs the field measurement method is commonly used. Nevertheless, since these methods inspect the anomalies by measuring the electrical properties such as split-voltage, insulation resistance and electric field of the insulator, they are unable to detect a crack of the insulator that is caused by repetitive mechanical and thermal stresses or a damage that is caused by a physical external force.

SUMMARY

The present invention provides a nondestructive inspection method of testing insulators using frequency resonance function that can also detect a mechanical defect such as a crack or damage of an insulator being inspected by evaluating the integrity of the insulator through the measurement of physical quantities of the insulator.

An aspect of the present invention provides a nondestructive inspection method of testing insulators using a frequency resonance function that includes vibrating an inspector and measuring the magnitude of a vibration force and the motion of the inspector according to the vibration, in which the vibration force is inputted when vibrated, converting the magnitude of the measured vibration force and the motion of the inspector to a first frequency resonance function, and determining whether the insulator has an anomaly according to a difference between modes and amplitudes of the first frequency resonance function and a second frequency resonance function by comparing the first frequency resonance function with the second frequency resonance function, which is a frequency resonance function of a normal insulator.

The vibration can be performed by using an impact hammer or vibrator.

The magnitude of the vibration force can be measured by a force detector, and the motion of the insulator can be measured by at least one of an accelerometer, a speedometer, a displacement-meter and a microphone.

The method can further include applying a rectangular window function to the measured magnitude of the vibration force and applying an index window function to the measured motion of the insulator.

The method can further include selecting a mode being measurable through a mode shaped analysis of the insulator.

Additional aspects and advantages of the present invention will be set forth in part in the description which follows, and in part will be obvious from the description, or may be learned by practice of the invention.

BRIEF DESCRIPTION OF THE DRAWINGS

FIGS. 3A to 5B are graphs illustrating the results of mode shaped analyses of an insulator according to a nondestructive inspection method of testing insulators using frequency resonance function, wherein FIGS. 3A and 3B are graphs illustrating the results of a first mode shaped analysis of an insulator, FIGS. 4A and 4B are graphs illustrating the results of a second mode shaped analysis of an insulator, and FIGS. 5A and 5B are graphs illustrating the results of a third mode shaped analysis of an insulator;

FIGS. 6A and 6B briefly show an experiment for selecting the range of a normal mode for an insulator according to a nondestructive inspection method of testing insulators using frequency resonance function, wherein FIG. 6A shows seven insulators that are serially arranged, and FIG. 6B is a plan view illustrating eight points displayed on an insulator in a fourth row from the top among the seven insulators;

FIGS. 8A and 8B show another example of frequency resonance function that is measured by vibrating an abnormal insulator according to a nondestructive inspection method of testing insulators using frequency resonance function.

DETAILED DESCRIPTION

Figure 1:
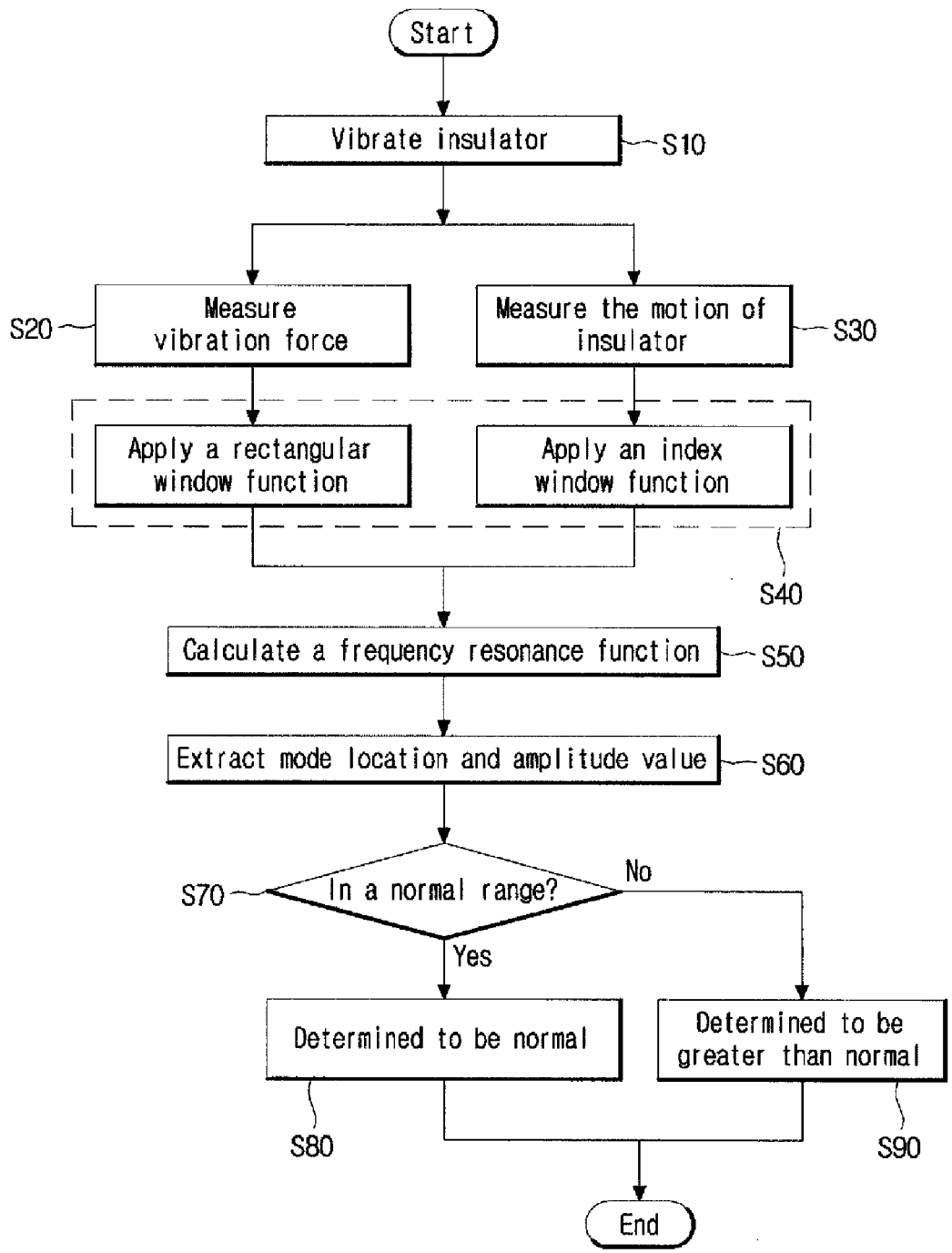
FIG. 1 is a flowchart illustrating a nondestructive inspection method of testing insulators using frequency resonance function.

A nondestructive inspection method of testing insulators using frequency resonance function according to certain embodiments of the present invention will be described below in more detail with reference to the accompanying drawings. Throughout the drawings, similar elements are given similar reference numerals. All terms, including technical terms and scientific terms, used herein have the same meaning as how they are generally understood by those of ordinary skill in the art to which the present invention pertains. Any term that is defined in a general dictionary shall be construed to have the same meaning in the context of the relevant art, and, unless otherwise defined explicitly, shall not be interpreted to have an idealistic or excessively formalistic meaning.

Since there can be a variety of permutations and embodiments of the present invention, certain embodiments will be illustrated and described with reference to the accompanying drawings. This, however, is by no means to restrict the present invention to certain embodiments, and shall be construed as including all permutations, equivalents and substitutes covered by the spirit and scope of the present invention.

Prior to the description of the present invention, the principle of a nondestructive inspection method of testing insulators using frequency resonance function will be briefly described below.

While an insulator is used in a high-voltage state for a long time, it is exposed to various negative environments such as mechanical or thermal fatigue loads. A method for the nondestructive testing of insulators using frequency resonance function is developed to determine whether the insulator has an anomaly that may be caused by the ones described above. When a defect occurs in the insulator, a mass or rigidity factor is changed, as shown in the following mathematical equation 1. The nondestructive inspection method of testing insulators using frequency resonance function inspects the anomaly of the insulator by detecting the change in location and amplitude of natural frequency of the system.

$$f = \frac{1}{2\pi}\sqrt{\frac{k + \Delta k}{m + \Delta m}} \qquad \text{[Mathematical Equation 1]}$$

Here, f is natural frequency, k is rigidity, $\Delta k$ is a change in rigidity, m is mass and $\Delta m$ is a change in mass.

To determine the properties of such system, a frequency resonance function, like the following mathematical equation 2, can be used. To extract the frequency resonance function, the insulator is initially vibrated by using an impact hammer or vibrator, and then a vibration force being inputted is measured by, for example, a force detector. Also, a response from the insulator is measured by, for example, using an accelerometer, speedometer, displacement-meter and microphone.

$$FRF = \frac{P_{xy}(f)}{P_{xx}(f)} \qquad \text{[Mathematical Equation 2]}$$

Here, Pxx(f) is the power spectral density (PSD) of the measured vibration force, and Pxy(f) is the cross-power spectral density of motion information of the insulator and the vibration force.

By the frequency resonance function, the magnitude of motion of the insulator per unit force in each frequency can be measured, and thus it is possible to inspect the insulator. In other words, the nondestructive inspection method of testing insulators using frequency resonance function can also inspect a mechanical defect such as a crack or damage of the inspector by vibrating the insulator with a force having the characteristic of white noise, measuring the change in motion of the insulator according to the vibration, calculating the frequency resonance function of the insulator and inspecting an anomaly of the insulator based on the ones described above.

An example of the nondestructive inspection method of testing insulators using frequency resonance function will be described below with reference to the accompanying drawings.

FIG. 1 is a flowchart illustrating a nondestructive inspection method of testing insulators using frequency resonance function.

Referring to FIG. 1, an insulator is vibrated by a vibration force having the characteristic of white noise (S10), and at this time the vibration force being inputted is measured (S20). At the same time, the motion of the insulator is measured by using a sensor such as an accelerometer, speedometer, displacement-meter or microphone (S30). Here, a window function can be applied to the measured signal to improve the quality of the signal (S40). For instance, a rectangular window function can be applied to a force signal representing the vibration force, and an index widow function can be applied to a sound pressure signal representing the motion information of the insulator measured by using the microphone.

A frequency resonance function is calculated by using the mathematical equation 2 (S50), and the mode location and amplitude value of a measurable mode is extracted from the calculated frequency resonance function (S55). Whether the insulator has an anomaly or not is inspected by using the calculated mode location and amplitude value (S60). The calculated mode location and amplitude value are inputted into an insulator inspection robot to which the present invention is applied, and then the anomaly of the insulator is inspected by checking whether the extracted mode location, i.e., a natural mode, of the insulator is at a normal location and whether the amplitude value has a normal amplitude.

For a further description, the term "mode" used herein is referred to as a resonant frequency, which occurs because there are several natural frequencies if the degree of a certain system is expressed as having at least three degrees, while the natural frequency is referred to as a frequency creating resonance when a certain system is vibrated if the degree of the system is expressed as having at least two degrees.

In this inspection, it can be determined whether a frequency resonance function calculated from an insulator to be inspected is within the range of frequency resonance function of a normal insulator ("normal range" hereinafter) by comparing the mode and amplitude of the frequency resonance function calculated from the insulator to be inspected with the mode and amplitude of the frequency resonance function calculated from the normal insulator.

If the mode location and amplitude value of the insulator to be inspected are within the normal range, it is determined that they are normal (S70), and if not within the normal range, it is determined that they are equal to or greater than normal (S80).

The nondestructive inspection method of testing insulators using frequency resonance function will be described in more detail with reference to FIGS. 2 and 3 in which an insulator inspection robot to which the present invention is applied is illustrated.

Figure 2:
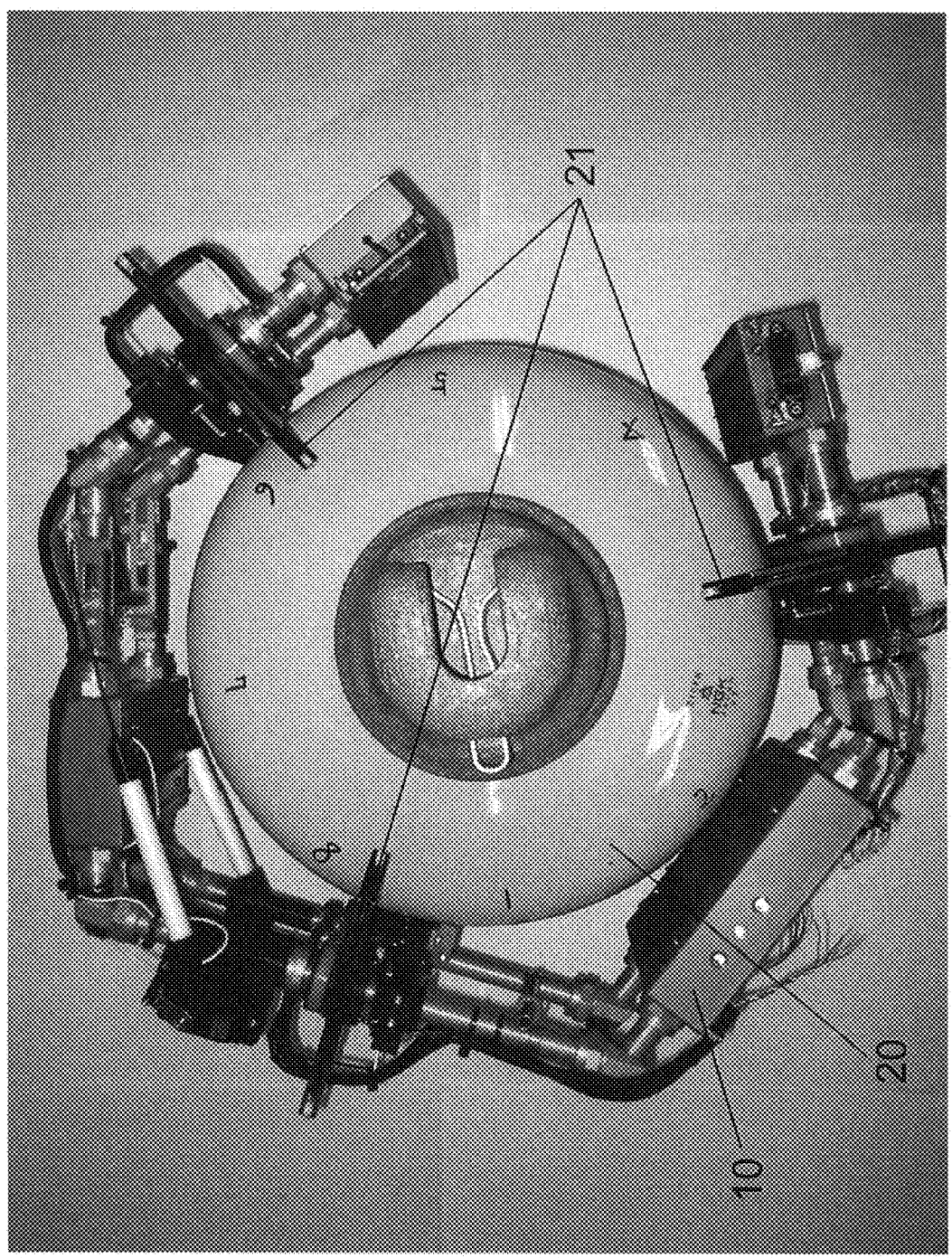
FIG. 2 shows an insulator inspection robot to which a nondestructive inspection method of testing insulators using frequency resonance function is applied.
Figure 3A:
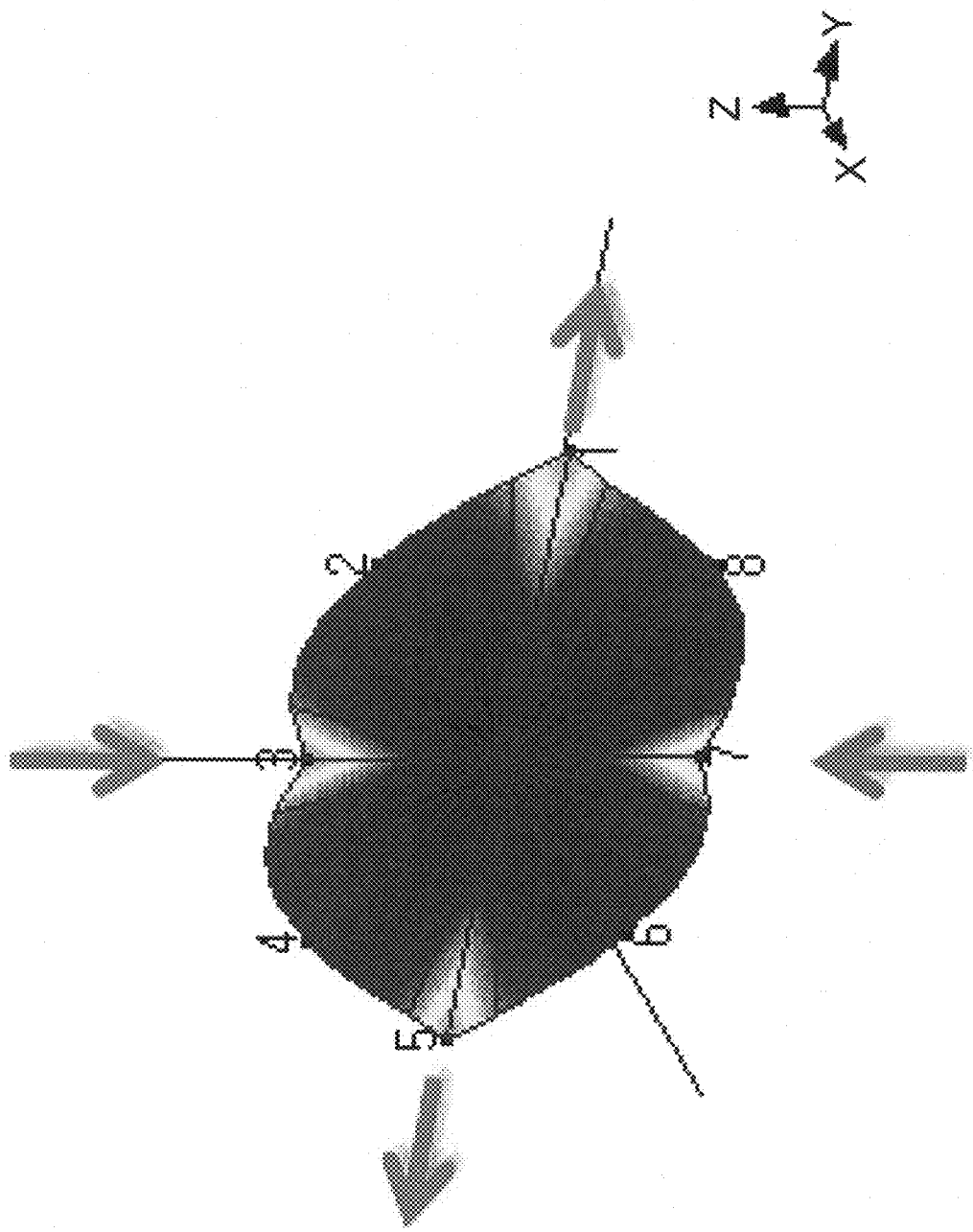
Figure 3B:
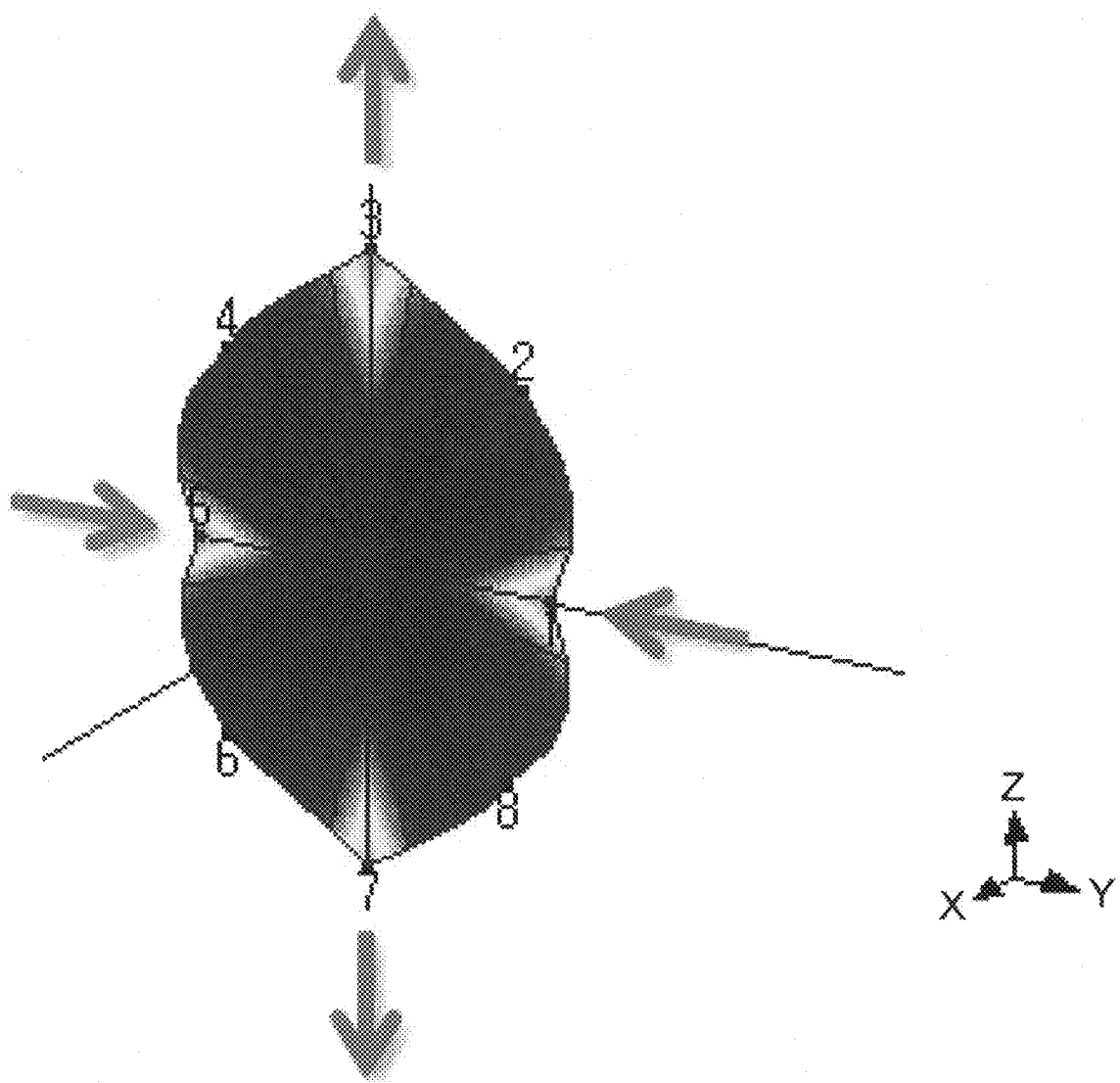
Figure 5B:
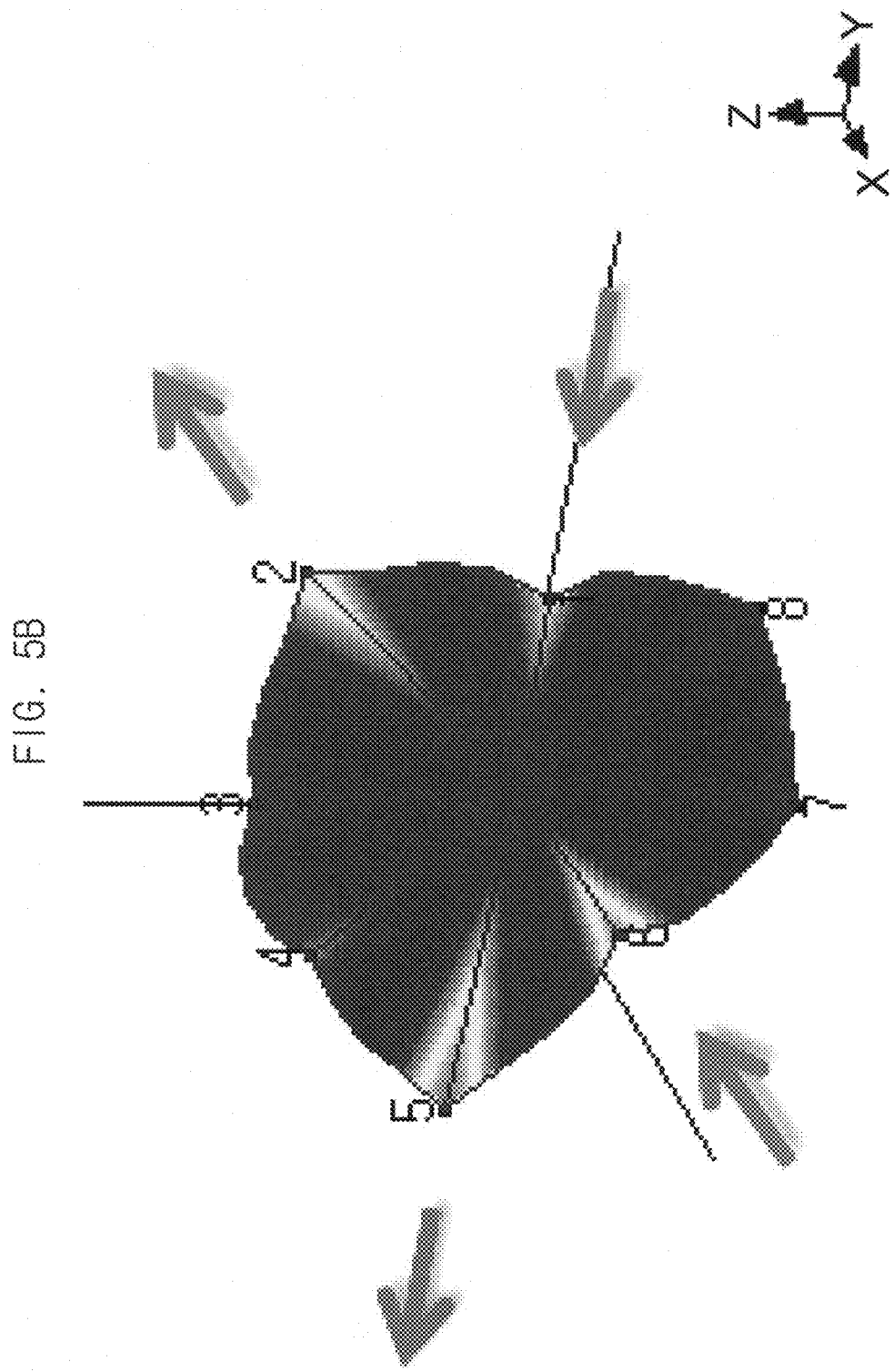

FIG. 2 shows an insulator inspection robot to which a nondestructive inspection method of testing insulators using frequency resonance function is applied. FIGS. 3A to 5B are graphs illustrating the results of mode shaped analyses of an insulator, FIGS. 3A and 3B are graphs illustrating the results of a first mode shaped analysis of an insulator, FIGS. 4A and 4B are graphs illustrating the results of a second mode shaped analysis of an insulator, and FIGS. 5A and 5B are graphs illustrating the results of a third mode shaped analysis of an insulator.

Referring to FIG. 2, an insulator inspection robot 10 is equipped with a vibrator (not shown) and a sensor (not shown), and a robot frame is coupled to an insulator 20 with a contact point 21 at an interval of 120° along its outer circumference. However, the number of the contact points and the angle between the contact points can vary depending on the number of the robot frames. Meanwhile, such restriction in which the insulator inspection robot 10 has to be coupled to the insulator 20 to measure can cause a change or restriction in mode shape of the insulator.

Thus, if the insulator inspection robot 10 is coupled to the insulator 20, the mode is restricted so that the inspection is impossible to perform. Thus, a preliminary process of determining whether mode extraction is possible or not is required by analyzing each shape of the modes even if the insulator inspection robot 10 is coupled to the insulator.

As an example of the insulator, a mode shape analysis of an NGK 210 kN insulator, which is most commonly used in a 345 kV transmission line, is performed.

In an experiment to analyze the mode shape, an insulator is vibrated by using an impact hammer, and the motion of the insulator is measured by using an accelerometer. Of course, it shall be apparent that a device to vibrate the insulator and a device to measure the motion of the insulator can vary in addition to the ones described above.

Considering the computational ability of a microprocessor installed in the insulator inspection robot 10, a frequency of interest is selected between 0 MHz and 5000 MHz. The frequency of interest is selected from a measurable range by considering the performance of CPU of the insulator inspection robot 10. The frequency of interest means a frequency range that the user wants to inspect.

As illustrated in FIGS. 3A to 5B, it can be seen that all three modes of the insulator are within the frequencies of interest. For the convenience of illustration, FIGS. 3A to 5B show the Y-axis and the Z-axis as the horizontal line and the X-axis as the vertical line. A first mode exists in a frequency of 1720 Hz. In this mode, as illustrated in FIGS. 3A and 3B, if points 1 and 5 on the Y-axis are extended, points 3 and 7 are decreased, and if the points 3 and 7 on the Z-axis are extended, the points 1 and 5 are decreased.

A second mode exists in a frequency of 3210 Hz. In this mode, as illustrated in FIGS. 4A and 4B, the insulator becomes wider and then smaller repeatedly on the horizontal plane. In a third mode, as illustrated in FIGS. 5A and 5B, if points 1 and 6 are extended, points 2 and 5 are decreased, and if the points 1 and 6 are decreased, the points 2 and 5 are extended.

Since the insulator inspection robot 10 restricts the insulator 20 at three supporting points, the second mode, in which the insulator becomes wider and smaller repeatedly on the horizontal plane, cannot be measured when the inspection is performed. Thus, in the present invention, the first and third modes are tested for the inspection of the insulator 20 only.

If the insulator is an ideal linear system, the mode locations and magnitudes of the insulator must exactly match one another. However, due to the change in material properties based on the manufacturing conditions such as a local change in temperature of a brazier during the manufacturing process, the types of materials and the fine change in ratio and the nonlinearity of the insulator, a small change in location and magnitude of each mode of the insulator can occur.

Since the nondestructive inspection method of testing insulators using frequency resonance function inspects an anomaly through the change in location and magnitude of natural mode of the insulator, the ranges of location and magnitude of the first and third modes, which are selected for a normal insulator, are selected to develop an inspection system. However, the above-described modes are some examples selected through the experiment, and it shall be apparent that various modes can be selected depending on the type of the insulator.

Figure 6A:
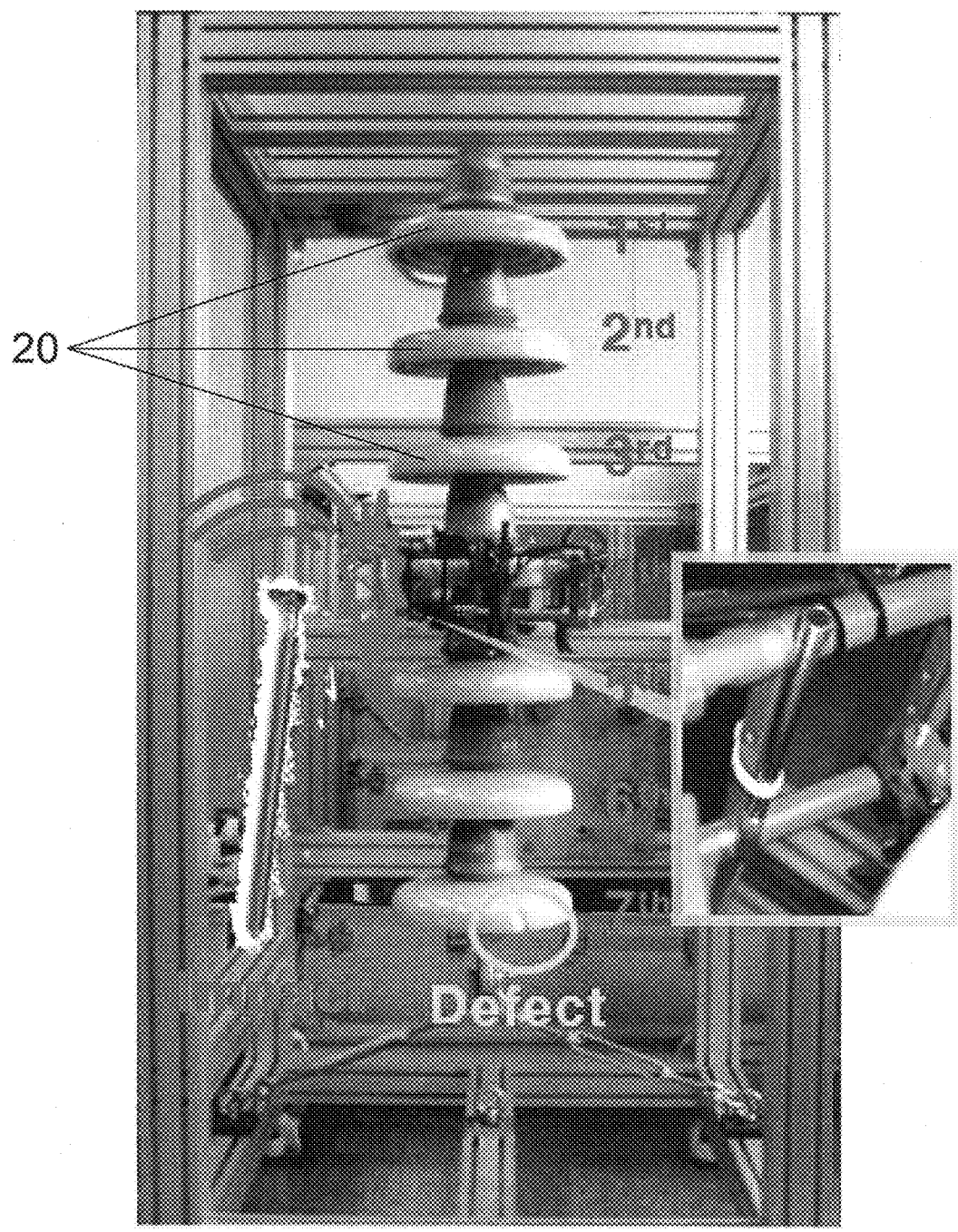
Figure 6B:
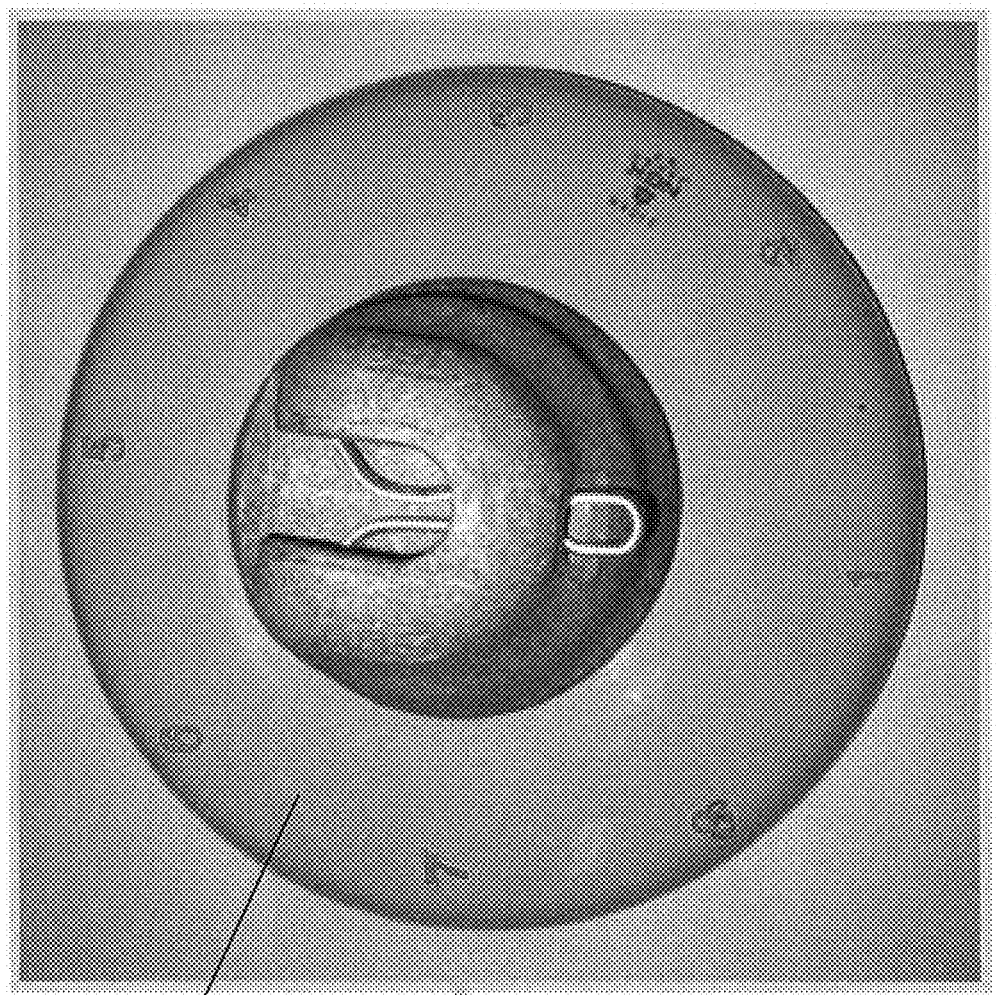
Figure 7A:
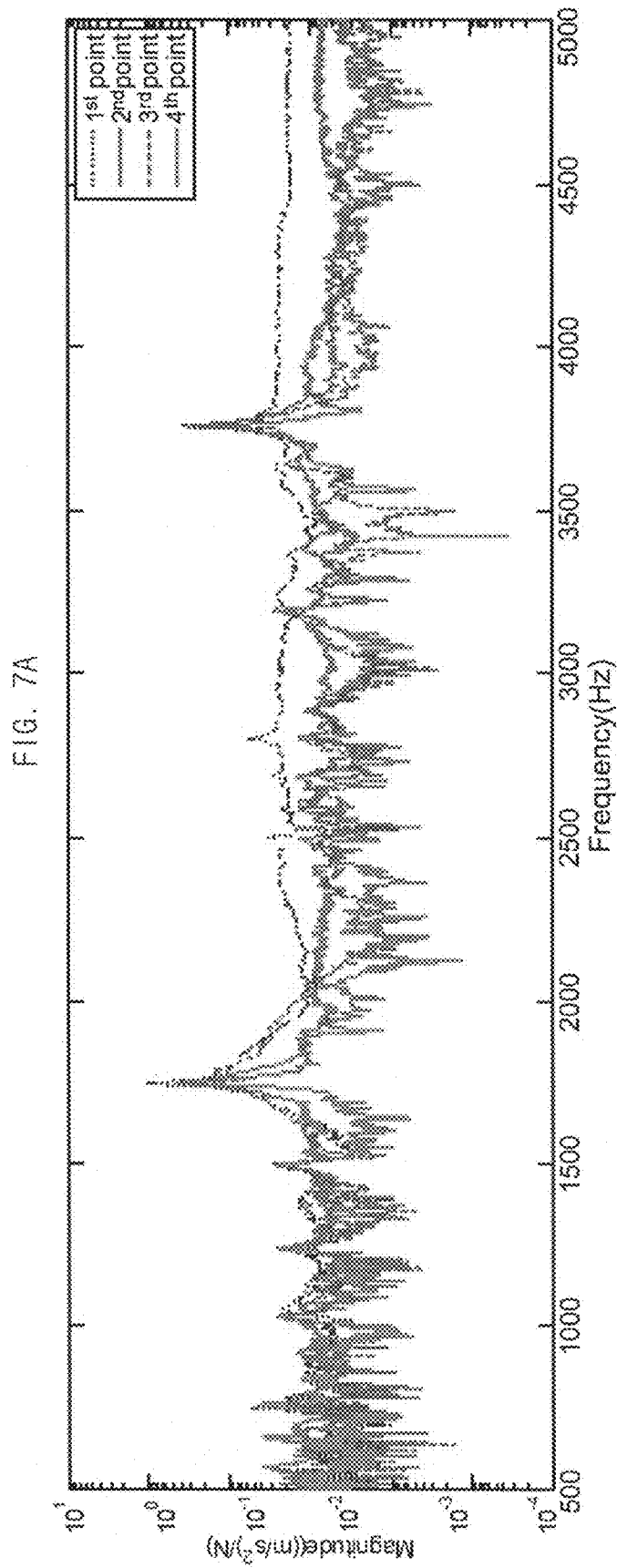
FIGS. 7A and 7B show an example of frequency resonance function that is measured by vibrating a normal insulator according to a nondestructive inspection method of testing insulators using frequency resonance function.
Figure 7B:
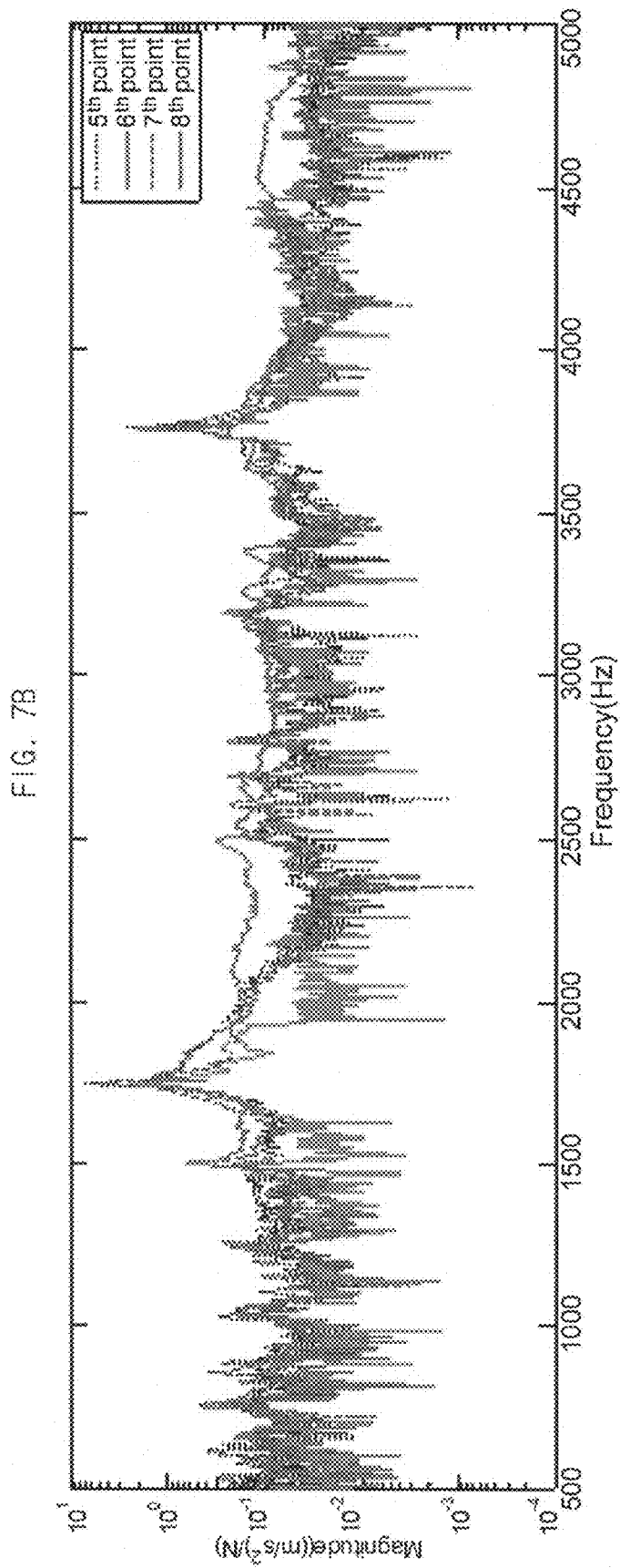

FIGS. 6A and 6B briefly show an experiment for selecting the range of a normal mode for an insulator according to a nondestructive inspection method of testing insulators using frequency resonance function, and FIGS. 7A and 7B show an example of frequency resonance function that is measured by vibrating a normal insulator according to a nondestructive inspection method of testing insulators using frequency resonance function. Referring to FIG. 6, an insulator is vibrated by using the impact hammer according to the experiment, and the motion of the insulator is measured by using the microphone. Here, seven suspension insulators 20a to 20g are serially connected to one another, like a thread line, and then eight points 21 to 28 marked on a fourth insulator 20d from the top are repeatedly vibrated and measured successively. Then, a total of 64 frequency resonance functions are measured.

In FIGS. 7A and 7B, the first to eighth points are vibrated successively, and a frequency resonance function that is measured from the first point 21 is shown as an example. Here, the first and third modes are observed relatively well, but it is difficult to observe the second mode because the insulator inspection robot 10 is restricted.

The following Table 1 shows the locations and magnitudes, i.e., amplitudes, of the first and third modes by organizing the experimental results.

TABLE 1

| | First mode | | | | Third mode | | | |
| | Maximum | | Minimum | | Minimum | | Maximum | |
| | Frequency | Magnitude | Frequency | Magnitude | Frequency | Magnitude | Frequency | Magnitude |
|---|---|---|---|---|---|---|---|---|
| First point | 1746 | 1.545 | 1750 | 10.346 | 3758 | 0.694 | 3772 | 3.614 |
| Second point | 1746 | 0.990 | 1774 | 7.988 | 3758 | 1.290 | 3768 | 3.096 |
| Third point | 1746 | 1.244 | 1786 | 8.171 | 3758 | 1.139 | 3772 | 3.692 |
| Fourth point | 1744 | 0.568 | 1752 | 6.607 | 3758 | 1.075 | 3768 | 3.433 |
| Fifth point | 1746 | 1.577 | 1786 | 11.364 | 3758 | 0.540 | 3770 | 4.572 |
| Sixth point | 1746 | 0.807 | 1744 | 6.085 | 3758 | 0.913 | 3770 | 0.731 |
| Seventh point | 1746 | 1.316 | 1748 | 10.014 | 3758 | 0.429 | 3774 | 3.491 |
| Eighth point | 1746 | 1.301 | 1754 | 11.233 | 3758 | 1.401 | 3770 | 2.747 |
| Max. | 1746 | 1.577 | 1786 | 11.364 | 3758 | 1.401 | 3774 | 4.572 |
| Min. | 1744 | 0.807 | 1748 | 6.085 | 3758 | 0.429 | 3768 | 2.731 |
| Difference (Max. − Min.) | 2 | 0.770 | 38 | 5.279 | 0 | 0.972 | 6 | 1.841 |

If the NGK 210 kN insulator used in the present experiment is, the location of the first mode can be selected between 1740 Hz and 1790 Hz, and the amplitude thereof can be selected between 0.9 and 11.5. Also, the location of the third mode can be selected between 3755 Hz and 3780 Hz, and the amplitude thereof can be selected between 0.4 and 4.6.

Figure 8B:
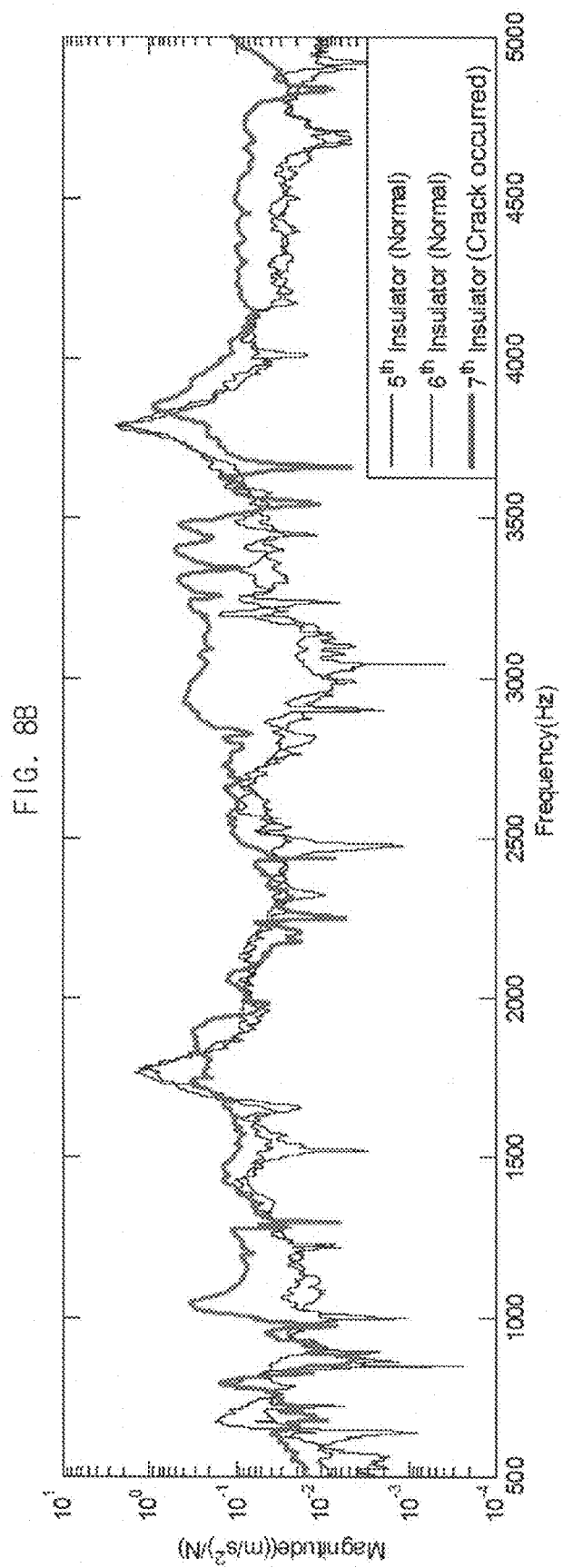

FIGS. 8A and 8B show another example of frequency resonance function that is measured by vibrating an abnormal insulator according to a nondestructive inspection method of testing insulators using frequency resonance function.

Referring to FIGS. 8A and 8B, a frequency resonance function that is measured by vibrating an abnormal insulator is shown, as compared to frequency resonance functions measured by vibrating the normal insulators. The following Table 2 shows the locations and magnitudes, i.e., amplitudes, of the first and third modes by organizing the experimental results by vibrating the abnormal insulator, like the ones described above.

TABLE 2

| | Microphone | | | |
| --- | --- | --- | --- | --- |
| | First mode | | Third mode | |
| | Frequency | Magnitude | Frequency | Magnitude |
| First insulator (normal) | 1770 | 0.8173 | 3762 | 0.7271 |
| Second insulator (normal) | 1776 | 2.4476 | 3770 | 2.5403 |
| Third insulator (normal) | 1778 | 0.8884 | 3778 | 1.3953 |
| Fourth insulator (normal) | 1782 | 1.2315 | 3772 | 2.0376 |
| Fifth insulator (normal) | 1784 | 1.2864 | 3766 | 2.4046 |
| Sixth insulator (normal) | 1786 | 1.5601 | 3758 | 2.2319 |
| Seventh insulator (clack occurred) | not appeared | not appeared | 3854 | 1.0111 |

To compare with a normal insulator, an abnormal insulator is installed in a seventh row inside an experimental device, as shown in FIG. 6, and the first to seventh insulators are vibrated successively so as to calculate their frequency resonance functions.

As it can be seen by looking at FIGS. 8A and 8B and Table 2, the first mode of the abnormal insulator is disappeared, and the mode location of the third mode thereof is not within the normal range.

As such, the nondestructive inspection method of testing insulators using frequency resonance function can inspect a mechanical defect of an insulator and readily determine an anomaly of the insulator if the range of an abnormal insulator exceeds the range of normal mode of a normal insulator when the normal mode of the normal insulator is determined against various forms and sizes of the insulator.

While the spirit of the present invention has been described in detail with reference to particular embodiments, the embodiments are for illustrative purposes only and shall not limit the present invention. It is to be appreciated that those skilled in the art can change or modify the embodiments without departing from the scope and spirit of the present invention.

What is claimed is:

1. A nondestructive inspection method of testing insulators using a frequency resonance function, the method comprising:
vibrating an inspector and measuring the magnitude of a vibration force and the motion of the inspector according to the vibration, the vibration force being inputted when vibrated;
converting the magnitude of the measured vibration force and the motion of the inspector to a first frequency resonance function; and
determining whether the insulator has an anomaly according to a difference between modes and amplitudes of the first frequency resonance function and a second frequency resonance function by comparing the first frequency resonance function with the second frequency resonance function, which is a frequency resonance function of a normal insulator.

2. The method of claim 1, wherein the vibration is performed by using an impact hammer or vibrator.

3. The method of claim 1, wherein the magnitude of the vibration force is measured by a force detector, and the motion of the insulator is measured by at least one of an accelerometer, a speedometer, a displacement-meter and a microphone.

4. The method of claim 1, further comprising applying a rectangular window function to the measured magnitude of the vibration force and applying an index window function to the measured motion of the insulator.

5. The method of claim 1, further comprising selecting a mode being measurable through a mode shaped analysis of the insulator.

6. The method of claim 1, wherein the mode is more than one mode.

7. The method of claim 1, wherein the frequency resonance function is calculated by the equation $$FRF = \frac{P_{xy}(f)}{P_{xx}(f)},$$

wherein Pxx(f) is the power spectral density (PSD) of the measured vibration force, and Pxy(f) is the cross-power spectral density of motion information of the insulator and the vibration force.

8. The method of claim 1, wherein at least one point of the insulator is vibrated.

9. The method of claim 8, wherein the first frequency resonance function is generated by converting the magnitude of the vibration force and the motion of the insulator measured when each of the insulator is vibrated.

10. The method of claim 1, wherein the determining of whether the insulator has an anomaly is a determining of normal if mode location and amplitude of the first frequency resonance function are within a range of location and amplitude of the second frequency resonance function.

* * * * *